United States Patent [19]
Gupta et al.

[11] Patent Number: 6,153,672
[45] Date of Patent: Nov. 28, 2000

[54] COMPOSITION OF TRIS-PYRROLIDONYL TRIAZINE AND POLYFUNCTIONAL ACTIVE H-CONTAINING MATERIAL

[75] Inventors: Ram B. Gupta, Bronx, N.Y.; Robert G. Lees, South Stamford, Conn.

[73] Assignee: Cytec Technology Corp., Wilmington, Del.

[21] Appl. No.: 08/001,697

[22] Filed: Jan. 7, 1993

Related U.S. Application Data

[63] Continuation of application No. 07/973,676, Nov. 9, 1992, abandoned, which is a continuation-in-part of application No. 07/793,077, Nov. 15, 1991, abandoned.

[51] Int. Cl.$^7$ ........................ C07D 403/14; C08G 73/06; C08L 33/14; C08L 67/02
[52] U.S. Cl. ........................ 523/414; 524/558; 524/589; 524/601; 525/328.2; 525/330.5; 525/437; 525/453; 525/523; 525/934; 528/367; 528/371; 544/198
[58] Field of Search ........................ 540/450, 484, 540/544; 544/180, 196, 200, 216, 198; 546/248; 548/304, 404, 473, 532; 564/117, 118, 120, 142, 143; 523/414; 524/558, 589, 601; 525/328.2, 330.5, 437, 453, 523, 934; 528/367, 371

[56] References Cited

U.S. PATENT DOCUMENTS

| | | | |
|---|---|---|---|
| 3,919,352 | 11/1975 | Iwasawa et al. | 524/100 |
| 4,002,699 | 1/1977 | Labana et al. | 524/512 |
| 4,352,924 | 10/1982 | Wooten et al. | 528/302 |
| 4,442,270 | 4/1984 | Passmore et al. | 524/904 |
| 4,777,213 | 10/1988 | Kanda et al. | 524/507 |
| 4,846,946 | 7/1989 | Mauer et al. | 204/181.4 |
| 4,939,213 | 7/1990 | Jacobs, III et al. | 528/45 |
| 4,959,482 | 9/1990 | Lee | 548/543 |
| 5,015,676 | 5/1991 | Macholdt et al. | 523/453 |

FOREIGN PATENT DOCUMENTS 58-146582  9/1983  Japan.

OTHER PUBLICATIONS

M.K. Akkapeddi et al, Polymer Preparations, vol. 27, No. 1, pp. 117–178 (1986).

M.K. Akkapeddi et al, Recent Advances in Anionic Polymerization, Proceedings of International Symposium of 1986, pp. 313–328 (1987).

Chemical Abstract, 1988, (Blokhina et al), Synthesis of N–aryl amino–2–pyrrolidones from Y–chlorobutyric acidhydrazines, CA 108:131479j.

Lipp etal. *Chemische Berichte*, 58, No. 6, pp. 1011–1014 (1925). (In German only).

Chemical Abstracts, 102, No. 6, p. 40, abstract No. 46729n, JP–A–59113019, (1985).

Chemical Abstracts, 79, No. 2, p. 80, abstract No. 6660t, JP–A–48000993, (1973).

*Primary Examiner*—Robert E. Sellers
*Attorney, Agent, or Firm*—Michelle A. Sherwood; Claire M. Schultz; Michael J. Kelly

[57] ABSTRACT

A process for preparing a tris-lactam crosslinking agent, tris-pyrrolidonyl triazine, from N,N',N"-tris(4-chlorobutyryl)melamine by treatment of the chlorobutyryl derivative with a base such as sodium or potassium carbonate to effect intramolecular cyclization to the tris-lactam. A curable composition comprised of tris-pyrrolidonyl triazine as the crosslinking agent and a hydroxyfunctional or aminofunctional material as a resin. Thick films with no pinholes are prepared from the curable compositions using powder coating techniques.

28 Claims, No Drawings

COMPOSITION OF TRIS-PYRROLIDONYL TRIAZINE AND POLYFUNCTIONAL ACTIVE H-CONTAINING MATERIAL

CROSS-REFERENCE TO RELATED APPLICATIONS

This application is a continuation of U.S. application Ser. No. 07/973,676, filed Nov. 9, 1992, now abandoned, which is a continuation-in-part of U.S. application Ser. No. 07/793,077, filed Nov. 15, 1991, now abandoned.

BACKGROUND OF THE INVENTION

1. Field of the Invention

This invention is directed to a process for preparing a triazine tris-lactam crosslinking agent, 2,4,6-tris-(pyrrolidin-2-on-1-yl)-1,3,5-triazine, hereinafter "tris-pyrrolidonyl triazine", and curable compositions containing the tris-pyrrolidonyl triazine crosslinking agent.

2. Related Background Art

Crosslinked materials have found widespread use in coatings such as powder coatings, solution coatings, coil coatings, can coatings, and in non-coatings applications such as conventional moldings, reactive injection moldings, composites, adhesives and binders. Because crosslinked materials find applications in widely different, increasingly diverse, and highly specialized areas, each such application has placed a new and usually unmet demand on the crosslinkers currently available or in use. There exists, therefore, a continuing need for new crosslinkers which are capable of meeting the requirements of a particular application.

The tris-pyrrolidonyl triazine crosslinking agent prepared by the process of this invention is capable of meeting demands that have not been met by existing crosslinkers.

Linear copolymers prepared from [bis-pyrrolidone-and tris]bis-pyrrolidone-substituted triazines have been disclosed by M. K. Akkapeddi et al in *Polymer Preparations,* Volume 27, Number 1, pages 177 to 178 (1986) and also in Recent Advances in Anionic Polymerizations, Proceedings of International Symposium of 1986, pages 313 to 328 (published in 1987). The copolymers disclosed therein, however, are linear block copolymers with no crosslinking present to give rise to a three dimensional crosslinked network.

JP 58146582 discloses the use of triazine tris-lactams as thermosetting resins material and as hardening agents for epoxy and phenolic resins.

It is an object of this invention to provide a process for the preparation of the tris-pyrrolidonyl triazine crosslinking agent.

It is another object of this invention to provide uncatalyzed and acid, base or organometallic compound catalyzed curable compositions containing a tris-pyrrolidonyl triazine crosslinking agent and active hydrogen-containing polyfunctional materials.

SUMMARY OF THE INVENTION

This invention is a novel process for the preparation of tris-pyrrolidonyl triazine crosslinking agent comprising contacting N,N',N"-tris(4-halobutyryl) melamine with a base.

This invention is also a curable composition containing (i) a tris-pyrrolidonyl triazine crosslinking agent, and (ii) an active hydrogen containing polyfunctional material. Thick films with no pinholes may be advantageously prepared from the curable compositions of this invention using powder coating techniques.

DETAILED DESCRIPTION OF THE INVENTION

I. PROCESS FOR PREPARING TRIS-PYRROLIDONYL TRIAZINE

Tris-pyrrolidonyl triazine is prepared by an intramolecular cyclization reaction of N,N', N"-tris(4-halobutyryl) melamine, which in turn is prepared by contacting N-halomelamines and 4-halobutyryl halide at a temperature and for a time sufficient to produce the desired starting material. The temperature for producing the N,N',N"-tris(4-halobutyryl)melamine starting material may range from about −20° C. to about 120° C. and is preferably about 70° C., while the time of the reaction is the range of about 10 minutes to 24 hours and is typically complete within a 2 to 20 hour period at about 70° C.

The starting material may be prepared by a continuous or batch process. It may be carried out by simply admixing the N-halomelamine and 4-halobutyryl halide, but is preferably carried out in a halogenated solvent, such as carbon tetrachloride.

As an example, N,N',N"-tris(4-chlorobutyryl)melamine starting material may be prepared by contacting N,N',N"-trichloromelamine (commercially available from Aldrich Chemical Company, Milwaukee, Wis. and also known as N,N',N"-trichloro-2,4,6-triamino-1,3,5-triazine) with 4-chlorobutyryl chloride in carbon tetrachloride solvent at a temperature of about 60° C. for approximately 2 to 8 hours. The resulting starting material may be separated and purified by recrystallization and filtration techniques well known to those skilled in the art. Other N,N',N"-tris(4-halobutyryl) melamine starting materials which may be used in the process of this invention may be prepared similarly, for example, by selecting another 4-halobutyryl halide, such as 4-bromobutyryl bromide. The preparation of the N,N',N"-tris(4-chlorobutyryl)melamine starting material used in the process of this invention is illustrated below:

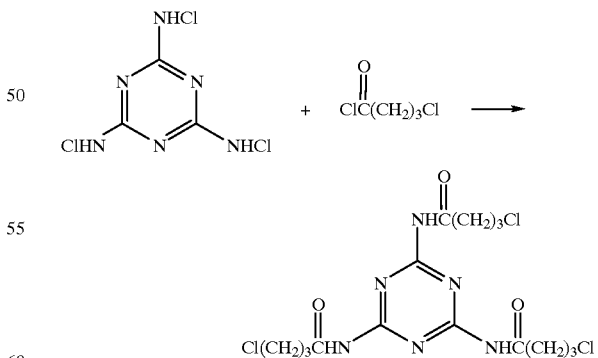

The novel process of this invention comprises contacting N,N',N"-tris(4-halobutyryl)melamine with a base at a temperature and for a length of time sufficient to produce tris-pyrrolidonyl triazine as the intramolecularly cyclized product. The chemical transformation is depicted below:

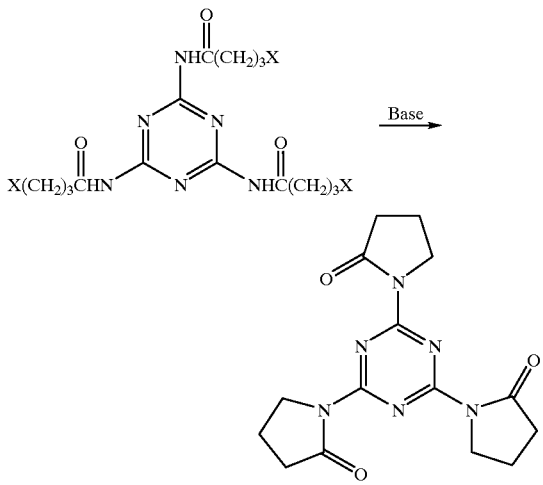

The group X above is a halogen selected from the group consisting of fluoro, chloro, bromo, iodo, mixtures thereof, and groups which are functionally equivalent to halogen groups such as those which are capable of serving as leaving groups during the intramolecular cyclization action leading to the tris-pyrrolidonyl triazine crosslinking agent.

Examples of such groups are methanesulfonate, benzenesulfonate, para-toluenesulfonate, trifluoromethanesulfonate, and the like. The term "halogen", therefore, as used in the context of this invention, includes non-halogen groups which are capable of functioning as leaving groups.

The preferred groups for X are chloro, bromo, iodo and mixtures thereof.

The base used in the practice of the process of the invention serves as the deprotonating agent for the N-H functionality and, thus, provides a driving force for the intramolecular cyclization reaction. The process is carried out typically in a base-unreactive non-protic solvent having a high dielectric constant capable of dissolving the various ionic intermediates at room temperature. The reaction may also be carried out in protic solvents, particularly when weaker bases are used. Suitable bases include organic, inorganic, and organometallic bases. Examples of organic bases are bases such as trialkylamines, aralkylamines, quaternary ammonium hydroxides and alkoxides, hindered tertiary amines, pyridine derivatives, bicyclic amines such as diazabicyclooctanes, and the like. Suitable inorganic bases include sodium or potassium hydride, sodium or potassium amide, sodium or potassium hydroxide, sodium or potassium carbonate, sodium or potassium alkoxide, and the like. Organometallic bases include organosodium, organopotassium, and organolithium reagents. Particularly useful are organolithium reagents such as n-butyl lithium, t-butyl lithium, phenyl lithium, lithium diisopropylamide, and the like. The use of inorganic bases, particularly inorganic bases such as hydrides, hydroxides, carbonates and alkoxides of sodium or potassium, such as potassium tert-butoxide, is preferred.

To facilitate the deprotonation reaction, a phase transfer catalyst may be used, however the reaction is usually carried out without the use of the phase transfer catalyst.

The process of the invention is preferably carried out at a temperature in the range of from about −20° C. to about 120° C., and a length of time from about 5 minutes to about 24 hours. However, it is usually sufficient to carry out the intramolecular cyclization reaction at 25° C. to 70° C. for a period of 2 to 20 hours only.

Among the advantages of the process of the invention are:
(a) availability of the starting N-halomelamines and 4-halobutyryl halides,
(b) convenient procedure, and
(c) high yield of the tris-lactam product, typically higher than 80% yield, versus the 30% reported yield for the alternative preparation reported in the article by A. K. Akkapeddi in *Polymer Preparations,* Vol. 27, No. 1, p. 177–178 (1986), cited above.

II. CURABLE COMPOSITIONS

The tris-pyrrolidonyl triazine is employed in the curable compositions of this invention as a crosslinking agent for polyfunctional active hydrogen-containing compounds, including hydroxyfunctional, aminofunctional, and mercaptofunctional materials contained in the curable compositions. The curable compositions containing the tris-pyrrolidonyl triazine and the polyfunctional active hydrogen-containing compounds may further comprise an acid, base, or organometallic cure catalyst, and may be used in solvent-based, water-based, or powder coatings. They may also be used as aqueous dispersions which are particularly suited to application by electrodeposition. They are thus useful in catalyzed or uncatalyzed, one component heat-cured systems for applications such as coatings, particularly powder coatings, coil coatings, and can coatings. They are also usable in non-coatings applications such as conventional moldings, reactive injection moldings, compositions, adhesives, and binders.

The novel curable composition of the invention comprises:
(i) tris-pyrrolidonyl triazines;
(ii) a polyfunctional active hydrogen-containing material; and optionally
(iii) a cure catalyst.

The polyfunctional active hydrogen-containing material comprises at least one class of active hydrogen functionally selected from the group consisting of hydroxy, amino, mercapto, and a group convertible thereto. The hydroxy and amino functional groups are preferred.

Illustrative examples of polyfunctional active hydrogen-containing materials are described in U.S. Pat. No. 5,846,946, the contents of which are incorporated herein by reference.

Especially suitable active hydrogen containing materials include polyesters, polyacrylates, and polyurethanes, all containing hydroxy groups as reaction sites. The preparation of polyesters, polyacrylates and polyurethanes is well known to those skilled in the art. For example, polyesters may be obtained by the reaction of polycarboxylic acids with excess quantities of polyhydric alcohols. It is known that polyacrylates may be obtained by the copolymerization of acrylic or methacrylic acid derivatives with hydroxy group-containing derivatives of these acids, such as, for example, the hydroxyalkylesters, optionally with the simultaneous use of additional vinyl compounds, such as, for example, styrene. It is also known that the hydroxy group-containing polyurethanes can be prepared by the reaction of polyisocyanates with excess quantities of compounds containing at least two hydroxy groups.

The cure catalyst is selected from the broad classes of catalysts such as acids, bases, and organometallic compounds. An example of a suitable acid catalyst is para-toluenesulfonic acid. An example of a suitable base catalyst is 2,2,2-diazabicyclooctane. An example of an organometallic cure catalyst is tetrabutyldiacetoxydistannoxane.

The acid cure catalysts usable in the invention include sulfonic acids such as para-toluenesulfonic acid, dinonyl naphthalenesulfonic acid, naphthalene sulfonic acid, dodecylbenzenesulfonic acid, mineral acids such as nitric and sulfuric, carboxylic acids such as oxalic, phosphoric acid, polyphosphoric acid, and the like. The use of para-toluenesulfonic acid is preferred.

The base cure catalysts usable in the invention include tertiary amines such as triethylamine, 2,2,2-diazabicyclooctane, N,N,-dimethylaniline, pyridine, dimethylaminopyridine, polydimethylaminopyridine, and the like. The use of 2,2,2-diazabicyclooctane is preferred.

The organometallic cure catalyst usable in the invention include organotin compounds and transition metal catalysts.

The organotin cure catalysts include dibutyltin di-2-ethylhexoate, dibutyltin diisooctyl maleate, dibenzyltin di-2-ethylhexoate, dibutyltin dilaurate, dimethyltin dilaurae, tetrabutyldiacetoxydistannoxane, tetramethyldiacetoxydistannoxane, tetrapropyldiacetoxydistannoxane and the like. Of the organotin compounds, tetrabutyldiacetoxydistannoxane (TBDAS) is preferred.

Suitable commercially available hydroxy group-containing polyesters are CYPLEX® 1531, a polyester of phthalic acid, adipic acid, ethanediol and trimethylolpropane from American Cyanamid Company, Cargil Polyester 5776 available from Cargil, and TONE® 0200 available for Union Carbide Corporation. Suitable hydroxy functional acrylic resins are available commercially from S. C. Johnson & Son, Inc. under the trademark JONCRYL® 500, a copolymer of 50% styrene, 20% hydroxypropyl methacrylate and 30% butyl acrylate, and from Rohm & Haas Co. under the trademark AT-400. Also suitable for use are hydroxy-terminated polycaprolactones.

The hydroxyfunctional polyfunctional active hydrogen-containing material comprises compounds and resins selected from acrylic resins, polyester resins, polyurethanes, polyols, products derived from the condensation of epoxy resins with an amine, and mixtures thereof.

The aminofunctional polyfunctional active hydrogen-containing material comprises compounds and resins selected from diamines such as ethylene diamine or hexamethylene diamine, from triamines, tetramines, polyamines, and mixture thereof.

A cure catalyst to accelerate the crosslinking reaction may be also optionally used, however, the tris-pyrrolidonyl triazine crosslinkers of the invention are capable of curing without the aid of an added catalyst.

When a catalyst is present, crosslinking takes place more rapidly at a particular temperature than when a catalyst is not present. Typically, crosslinking is effected at a lower temperature with a catalyst present.

The cure catalyst may also be a metal salt or a complex of a transition metal such as lead, zinc, iron, titanium, and manganese.

When employed, the cure catalyst is used in the tris-pyrrolidonyl triazine curable compositions in amounts effective to accelerate cure at the temperature employed. For example, the catalyst is typically used in amounts of from about 0.01 to about 2.0% by weight, with 0.02 to 1% metal, by weight, for the metal catalysts, based on the weight of the curable compositions.

In practice of the invention, the curable compositions can be adapted for use in solvent-based, water-based, and powder coating compositions when the tris-pyrrolidonyl triazine is employed.

The curable compositions of this invention give especially desirable and unexpected results when employed in powder coating techniques. It has been found that thick films that are substantially free of deleterious pin holes can be achieved by employing the inventive curable composition containing the tris-pyrrolidonyl triazine crosslinking agent in powder coatings. Powder coatings employing the curable composition of this invention may be prepared by methods well known to those skilled in the art. The curable coating compositions of this invention comprising aqueous dispersions are also particularly suited to application by electrodeposition.

Typically, the curable compositions will contain about 1 to 90 percent, by weight, of resin and crosslinker combined, and the weight of crosslinker and resin will range correspondingly from about 5 to about 50 parts of said crosslinker and from about 50 to 95 parts of said resin. Preferably, depending on the relative equivalent weights of the crosslinker and active hydrogen material, the weights would be from about 15 to 40 parts crosslinker and about 60 to 85 parts resin.

In many instances, a pigment composition and/or various other conventional additives such as antioxidants, surface active agents, coupling agents, flow control additives, and the like, are included. The pigment composition may be of any conventional type, such as iron oxides, lead oxides, strontium chromate, carbon black, titanium dioxide, talc, barium sulfate, cadmium yellow, cadmium red, chromic yellow, and the like.

After application to a substrate, such as a steel panel, the coating composition is cured by any conventional method, such as in baking ovens or with banks of infrared heat lamps.

Conventional methods may also be used to combine the novel curable composition of this invention with filler and/or reinforcements and to shape them into useful articles by means well known to accomplish these functions.

Crosslinked films or objects may be obtained by curing the curable compositions described above by allowing the curable compositions to crosslink either at room temperature or at elevated temperatures for a shorter period of time.

The following examples illustrative the various embodiments of the invention.

EXAMPLE 1

N,N',N"-Tris(4-Chlorobutyryl)Melamine From N,N',N"-Trichloromelamine

A mixture of 2.3 g N,N',N"-trichloromelamine, 20 ml carbon tetrachloride, 8.46 g 4-chlorobutyryl chloride and 30 mg N,N-dimethylaminopyridine was placed in a 100 ml flask fitted with a magnetic stirring bar, a reflux condenser and argon inlet. The reaction mixture was slowly heated in an oil bath to about 60° C. and was stirred at about 60° C. for 5 hours. It was allowed to cool down to room temperature and then diluted with 50 ml hexanes. The contents were stirred at room temperature for 30 minutes and then filtered. The residue was washed with hexane and dried under reduced pressure. It was characterized to be N,N',N"-tris(4-chlorobutyryl)melamine on the basis of NMR and mass spectroscopy (4.2 g; 95% yield):

$^1$H NMR (DMSO)-$d_6$, delta): 2.0 (m, 6H, 3× CH$_2$CH$_2$CH$_2$Cl), 2.8 (t, 6H 3× NHCOCH$_2$CH$_2$CH$_2$Cl), 3.6 (t, 6h, 3× CH$_2$CH$_2$Cl), 11.8 (broad s, 3H, 3× NHCO);

$^{13}$C NMR (DMSO-$d_6$, delta): 27, 34, 44, 161, 174; MASS (FAS, M+H$^+$): 439.

EXAMPLE 2

N,N',N"-tris-(4-chlorobutyryl)Melamine From Hexachloromelamine

A mixture of 3.33 g of hexachloromelamine, 8.46 g 4-chlorobutyryl chloride, carbon tetrachloride (20 ml), and 200 mg poly-dimethyl aminopyridine is heated at about 70° C. for 6 hours under argon. The carbon tetrachloride solvent is removed under reduced pressure. The residue is cooled and dissolved in a mixture for 50 ml methanol and 25 ml $CH_2Cl_2$. The mixture is then treated with 5 ml triethylamine dropwise while cooling. Next, the mixture is concentrated and the residue treated with methanol and filtered. The methanol is then removed under reduced pressure and the residue recrystallized from $CCl_4$/Hexane to give a product which is filtered and characterized to be identical with the product prepared from N,N',N"-trichloromelamine in Example 1, that is N,N',N"-tris(4-chlorobutyryl)melamine.

EXAMPLE 3

Preparation of 2,4,6-tris(pyrrolidin-2-on-1-yl)-1,3,5-triazine from N,N',N"-tris(4-chlorobutylryl) melamine.

Sodium hydride (200 mg, 60% in mineral oil) was placed in a flask fitted with an Argon inlet, a stopper, a rubber septum and a magnetic stirring bar. To it was added 5 ml n-hexane and the mixture allowed to stir for several minutes. Stirring was stopped and with the help of a syringe, n-hexane was removed. To the washed NaH thus obtained was added 5 ml dimethylformamide (DMF). The flask was cooled to about 0° C. in an ice-bath and 440 mg of N,N',N"-tris(4-chlorobutyryl)melamine, the product of Example 1, dissolved in 5 ml DMF was added with stirring to the flask containing NaH. Next, the reaction mixture was stirred at about 0° C. for 5 hours. The cooling bath was then removed and the reaction mixture allowed to warm to room temperature. The reaction mixture was then slowly added to 100 ml ice-cold water. The reaction mixture was extracted with $CH_2Cl_2$ (3×30 ml) and the dried over $MgSO_4$ (anhydrous). The $MgSO_4$ was filtered and the filtrate concentrated under reduced pressure. The solvent was then removed and the residue was dried under reduced pressure. The product was essentially a pure compound (270 mg, 82% yield) and was characterized to be 2,4,6-tris-(pyrrolidin-2-on-1-yl)-1,3,5-triazine by NMR and mass spectroscopy:

$^1$H NMR ($CDCl_3$, delta): 2.0 (m, 6H, 3× $CH_2CH_2$—$CH_2CO$), 2.6 (t, 6H, 3× $CH_2CH_2CO$), 4.0 (t, 6H, 3× $NCH_2CH_2$): MASS (FAB, M+H): 331.

EXAMPLE 4

Preparation of 2,4,6-tris(pyrrolidin-2-on-1-yl)-1,3,5-triazine from N,N',N"-tris(4-chlorobutyryl) melamine using potassium tertiary butoxide as a base 400 mg of N,N',N"-tris(4-chlorobutyryl)melamine was placed in a flask equipped with a magnetic stirring bar, a reflux condenser, an argon inlet and a rubber septum. To the flask was added 6 ml DMF followed by 450 mg potassium tert-butoxide, while stirring the reaction mixture at room temperature for about 30 minutes. It was then diluted with $CH_2Cl_2$ and filtered. The filtrate was concentrated to dryness under reduced pressure. The residue was then purified by column chromatography (silica gel) to give 180 mg of pure 2,4,6-tris(pyrrolidin-2-on-1-yl)-1,3,5-triazine.

EXAMPLE 5

Preparation of 2,4,6-tris(pyrrolidin-2-on-1-yl)-1,3,5-triazine from N,N',N"-tris(4-chlorobutyryl) melamine using potassium carbonate as base (solvent: Acetone/Toluene)

In a flask equipped with a magnetic stirring bar, a reflux condenser, an argon inlet, a rubber septum and a glass stopper was placed 10 gm of N,N',N"-tris(4-chlorobutyryl) melamine and 38 gm of anhydrous $K_2CO_3$. To it was added 150 ml acetone and 250 mg KI. The reaction mixture was heated in an oil bath at about 65–70° C. for 12 hours. Next, 50 ml toluene was added to the reaction mixture and heating was continued at about 80° C. for 12 hours. The reaction mixture was cooled to room temperature and 250 ml $CH_2Cl_2$ was added to it. The reaction mixture was then stirred for 3 hours at room temperature. It was then filtered through HIFLO, the residue washed with 100 ml $CH_2Cl_2$ and the combined filtrate concentrated to dryness to give 6.25 gm of the product analyzed to be 2,4,6-tris(pyrrolidin-2-on-1-yl)-1,3,5-triazine.

EXAMPLE 6

Preparation of 2,4,6-tris(pyrrolidin-2-on-1-yl)-1,3,5-triazine from N,N',N"-tris(4-chlorobutyryl) melamine using potassium carbonate as base (solvent: DMF)

In a flask equipped with a magnetic stirring bar, a rubber septum, a glass stopper, a reflux condenser and an argon inlet was placed 22.0 gm of N,N',N"-tris(4-chlorobutyryl) melamine and 62.0 gm of anhydrous $K_2CO_3$. To it was added 325 ml of DMF and the reaction mixture heated in an oil bath at about 75° C. under vigorous stirring for 6 hours. Next, it was heated at about 55° C. for 16 hours and then at about 75° C. for 4 hours. The reaction mixture was cooled to room temperature and diluted with 300 ml $CH_2Cl_2$ and stirred overnight (about 14 hours) at room temperature. The reaction mixture was filtered through HIFLO and the residue washed with $CH_2Cl_2$. The combined filtrate was concentrated to dryness under reduced pressure to give 13.6 gm of a product identified to be 2,4,6-tris(pyrrolidin-2-on-1-yl)-1,3,5-triazine.

EXAMPLE 7

Reaction of 2,4,6-tris(pyrrolidin-2-on-1-yl)-1,3,5-triazine with ethylene diamine: Formation of a polyamide by crosslinking To a solution of 33 mg of 2,4,6-tris-(pyrrolidin-2-on-1-yl)-1,3,5-triazine in 1 ml of $CH_2Cl_2$ was added to 10 mg ethylene diamine in 0.2 ml of $CH_2Cl_2$. The mixture was warmed to about 45° C. and then left at room temperature overnight. After 20 hours at room temperature, a gel material had formed. Thin layer chromagraphic (TLC) analysis of the reaction mixture revealed:

(1) the absence of ethylene diamine or tris-pyrrolidonyl triazine starting materials, and (2) the formation of a product which did not move on the TLC plates upon elution with an organic solvent.

Both observations are consistent with the formation of a crosslinked polymeric polyamide product.

EXAMPLE 8

Two coated panels, COATING A and COATING B, were prepared and evaluated as follows:

Cargill 3000 polyester resin, tris-pyrrolidonyl triazine, benzoin, R-960 pigment and Resiflow P-67 flow control agent were dry blended in a Waring blender in quantities specified in TABLE 1. The dry-blended powder was then melt mixed at about 90° C. to about 135° C. for 1–5 minutes in a two roll mill to allow homogeneous mixing without allowing crosslinking to occur. the melt-mixed material was then chopped into smaller pieces in a blender mill and fed into a mill classifier where the chips were ground to a find powder with particle size of about 35 microns. The finely ground powder, charged with up to 80 KV power, was thereafter sprayed in an electrostatic spray booth through an electrostatic spray gun on a grounded metal substrate such as Bonderite® 1000 substrate, a product of Parker Industries, Inc., hereinafter BO 1000.

The powder coated panels were each baked in an oven at the specified temperature (see TABLE 1) to allow the powder to fuse, flow out, and crosslink. The film and resistance properties of the resulting cured coatings, COATINGS A and COATING B, are summarized in TABLE 1. The results in TABLE 1 show that thick films containing no pinholes were obtained when cured at 175° C.–190° C. for 20 minutes (COATINGS A and B). Furthermore, films with good solvent resistance and hardness were obtained in both COATING A and COATING B demonstrating the advantageous utility of tris-pyrrolidonyl triazine as a crosslinking agent in powder coatings.

TABLE 1

POWDER COATINGS WITH TRIS-PYRROLIDONYL TRIAZINE AND CARGILL 3000 POLYESTER RESIN

| FORMULATION AND CURE | FORMULATION A | FORMULATION B |
| --- | --- | --- |
| Cargill 3000 Polyester (g) | 88.0 | 88.0 |
| Tris-pyrrolidonyl Triazine (g) | 12.0 | 12.0 |
| Benzoin Additive (g) | 1.4 | 1.4 |
| R 960 $TiO_2$ Pigment (g) | 40.0 | 40.0 |
| Resiflow P-67 (g) | 1.3 | 1.3 |
| Substrate | BO 1000 | BO 1000 |
| Bake Temperature (° C.) | 175 | 190 |
| Bake Time (min) | 20 | 20 |
| FILM AND RESISTANCE PROPERTIES | COATING A | COATING B |
| Film Appearance | Slightly Textured NO PINHOLES | Slightly Textured NO PINHOLES |
| Thickness (mm) | 0.046–0.064 | 0.046–0.74 |
| Hardness $HN_{25}$ | 12.4 | 18.2 |
| Pencil Hardness | 2H-H | 2H-H |
| Impact Front/Reverse (in.lb) | 20–30/0–5 | 0–5/0–5 |
| Color (Tristimulus) | 0.10 | 0.12 |
| Yellow Index | 5.11 | 7.17 |
| Gloss 60° | 76.5 | 73.6 |
| 20° | 34.2 | 48.4 |
| MEK Double Rubs | 120/200+ | 175/200+ |
| Humidity Resistance (60° C.) | Loss of gloss after 504 hrs. | Loss of gloss after 504 hrs. |

Although the present invention has been described with reference to certain preferred embodiments, it is apparent that modifications and variations thereof may be made by those skilled in the art without departing from the scope of this invention as defined by the appended claims.

What is claimed is:

1. A curable composition comprising:
   (i) tris-pyrrolidonyl triazine; and
   (ii) a polyfunctional active hydrogen containing material
   (iii) comprising hydroxyfunctional resins selected from the group consisting of polyesters, polyacrylates and polyurethanes.

2. The curable composition as recited in claim 1 further comprising an effective amount of a cure catalyst.

3. The curable composition as recited in claim 2 wherein the cure catalyst is selected from group consisting of acids, bases, and organometallic compounds.

4. The curable composition as recited in claim 1, comprising from about 5 to about 50 parts by weight of the tris-pyrrolidonyl triazine and from about 50 to about 95 parts by weight of the a polyfunctional active hydrogen containing material, based upon 100 parts by weight of the combination.

5. A powder coating composition comprised of a curable composition comprising:
   (i) tris-pyrrolidonyl triazine; and
   (ii) a polyfunctional active hydrogen containing material.

6. The powder coating composition as recited in claim 5 wherein the polyfunctional active hydrogen-containing material comprises at least one class of active hydrogen functionality selected from the group consisting of hydroxy, amino, mercapto and a group convertible thereto.

7. The powder coating composition as recited in claim 6 wherein the polyfunctional active hydrogen-containing material comprises hydroxyfunctional compounds and resins selected from the group consisting of acrylic resins, polyester resins, polyurethanes, products of condensation of epoxy resins with amines, and mixtures thereof.

8. The powder coating composition as recited in claim 5 further comprising an effective amount of a cure catalyst.

9. The powder coating composition as recited in claim 8 wherein the cure catalyst is selected from the group consisting of acids, bases, and organometallic compounds.

10. The powder coating composition as recited in claim 5, comprising from about 5 to about 50 parts by weight of the tris-pyrrolidonyl triazine and from about 50 to about 95 parts by weight of the a polyfunctional active hydrogen containing material, based upon 100 parts by weight of the combination.

11. A curable composition comprising:
    (i) tris-pyrrolidonyl triazine; and
    (ii) a polyfunctional active hydrogen containing material comprising amino active hydrogen functionality or a group convertible thereto.

12. The curable composition as recited in claim 11 wherein the polyfunctional active hydrogen-containing material comprises aminofunctional compounds and resins selected from the group consisting of diamines, triamines, tetramines, polyamines other than said diamines, triamines and tetramines, and mixtures thereof.

13. The curable composition as recited in claim 12 wherein the aminofunctional resin is ethylenediamine or hexamethylene diamine.

14. The curable composition as recited in claim 11 further comprising an effective amount of a cure catalyst.

15. The curable composition as recited in claim 11, comprising from about 5 to about 50 parts by weight of the tris-pyrrolidonyl triazine and from about 50 to about 95 parts by weight of the a polyfunctional active hydrogen containing material, based upon 100 parts by weight of the combination.

16. A water-based coating composition comprised of a curable composition comprising:
    (i) tris-pyrrolidonyl triazine; and
    (ii) a polyfunctional active hydrogen containing material.

17. The water-based coating composition as recited in claim 11 wherein the polyfunctional active hydrogen-containing material comprises at least one class of active hydrogen functionality selected from the group consisting of hydroxy, amino, mercapto and a group convertible thereto.

18. The water-based coating composition as recited in claim 17 wherein the polyfunctional active hydrogen-containing material comprises hydroxyfunctional compounds and resins selected from the group consisting of acrylic resins, polyester resins, polyurethanes, polyols, products of condensation of epoxy resins with amines, and mixtures thereof.

19. The water-based coating composition as recited in claim 16 further comprising an effective amount of a cure catalyst.

20. The water-based coating composition as recited in claim 16, comprising from about 5 to about 50 parts by weight of the tris-pyrrolidonyl triazine and from about 50 to about 95 parts by weight of the a polyfunctional active hydrogen containing material, based upon 100 parts by weight of the combination.

21. An electrodeposition coating composition comprised of an aqueous dispersion of a curable composition comprising:
    (i) tris-pyrrolidonyl triazine; and
    (ii) a polyfunctional active hydrogen containing material.

22. The electrodeposition coating composition as recited in claim 21 wherein the polyfunctional active hydrogen-containing material comprises at least one class of active hydrogen functionality selected from the group consisting of hydroxy, amino, mercapto and a group convertible thereto.

23. The electrodeposition coating composition as recited in claim 22 wherein the polyfunctional active hydrogen-containing material comprises hydroxyfunctional polyurethanes, polyols, products of condensation of epoxy resins with amines, and mixtures thereof.

24. The electrodeposition coating composition as recited in claim 21 further comprising an effective amount of a cure catalyst.

25. The electrodeposition coating composition as recited in claim 21, comprising from about 5 to about 50 parts by weight of the tris-pyrrolidonyl triazine and from about 50 to about 95 parts by weight of the a polyfunctional active hydrogen containing material, based upon 100 parts by weight of the combination.

26. The curable composition as recited in claim 2, wherein the effective amount of cure catalyst comprises at least about 0.01% based on the weight of the curable composition.

27. The powder coating composition as recited in claim 8, wherein the effective amount of cure catalyst comprises at least about 0.01% based on the weight of the curable composition.

28. The curable composition as recited in claim 14, wherein the effective amount of cure catalyst is at least about 0.01% based on the weight of the curable composition.

* * * * *